United States Patent
Kusuoka

(10) Patent No.: US 12,303,713 B2
(45) Date of Patent: May 20, 2025

(54) TREATMENT PREPARATION APPARATUS COMPRISING A PERIPHERAL SIMULATOR AND TREATMENT EQUIPMENT FOR A BORON NEUTRON CAPTURE THERAPY (BNCT)

(71) Applicant: SUMITOMO HEAVY INDUSTRIES, LTD., Tokyo (JP)

(72) Inventor: Shinya Kusuoka, Ehime (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 504 days.

(21) Appl. No.: 17/704,758

(22) Filed: Mar. 25, 2022

(65) Prior Publication Data

US 2022/0310244 A1 Sep. 29, 2022

(30) Foreign Application Priority Data

Mar. 26, 2021 (JP) ................. 2021-053309

(51) Int. Cl.
*A61N 5/10* (2006.01)
*G16H 20/40* (2018.01)
(Continued)

(52) U.S. Cl.
CPC ........... *A61N 5/103* (2013.01); *A61N 5/1048* (2013.01); *A61N 5/1049* (2013.01);
(Continued)

(58) Field of Classification Search
CPC ........ A61N 5/10; A61N 5/103; A61N 5/1048; A61N 5/1049; A61N 2005/105;
(Continued)

(56) References Cited

U.S. PATENT DOCUMENTS

| | | | |
|---|---|---|---|
| 6,094,760 A | * | 8/2000 | Nonaka .................... A61N 5/10 5/601 |
| 7,188,999 B2 | * | 3/2007 | Mihara ................ A61N 5/1082 378/197 |

(Continued)

FOREIGN PATENT DOCUMENTS

| | | |
|---|---|---|
| CN | 109011221 A | 12/2018 |
| CN | 109464752 A | 3/2019 |

(Continued)

OTHER PUBLICATIONS

An English translation of CN109011221A (Year: 2024).*
Office Action Issued in Taiwan Application No. 111110802, dated Jan. 7, 2023.

*Primary Examiner* — Allen C. Ho
(74) *Attorney, Agent, or Firm* — Michael Best & Friedrich LLP

(57) ABSTRACT

A treatment preparation apparatus includes a peripheral simulator that simulates a peripheral portion of the object after the object is disposed in the irradiation chamber, when fixing the relative position of the object to the irradiation target in the preparation chamber. Therefore, when positioning the patient in the preparation chamber, by using the peripheral simulator, the positioning can be performed in consideration of the peripheral portion of the object in the irradiation chamber. That is, in the preparation chamber, the patient can be fixed at a position in the irradiation chamber where shift is unlikely to occur, considering the positional relationship between the patient and the peripheral portion. From the above, when positioning the patient in the preparation chamber, it is possible to position the patient at a position that shift is unlikely to occur during irradiation.

9 Claims, 5 Drawing Sheets

(51) Int. Cl.
*G16H 40/63* (2018.01)
*A61B 90/00* (2016.01)

(52) U.S. Cl.
CPC ......... *A61N 5/1075* (2013.01); *A61N 5/1077* (2013.01); *A61N 5/1078* (2013.01); *G16H 20/40* (2018.01); *G16H 40/63* (2018.01); *A61B 2090/3945* (2016.02); *A61N 2005/109* (2013.01)

(58) Field of Classification Search
CPC .... A61N 2005/1056; A61N 2005/1059; A61N 2005/1063; A61N 5/1075; A61N 5/1077; A61N 5/1078; A61N 2005/109
USPC ............................ 378/65, 204, 205, 207–209
See application file for complete search history.

(56) References Cited

U.S. PATENT DOCUMENTS

| | | | | |
|---|---|---|---|---|
| 7,239,684 B2 * | 7/2007 | Hara | ................... | A61N 5/1049 378/65 |
| 8,283,645 B2 * | 10/2012 | Güneysel | ................ | G21F 7/005 250/517.1 |
| 9,399,147 B2 * | 7/2016 | Haruna | ................... | G21F 7/005 |
| 9,889,320 B2 * | 2/2018 | Liu | ......................... | H05H 3/06 |
| 10,155,123 B2 * | 12/2018 | Mukawa | ................... | G01T 1/29 |
| 10,157,693 B2 * | 12/2018 | Liu | ......................... | A61N 5/10 |
| 10,328,286 B2 * | 6/2019 | Liu | ......................... | G21G 4/02 |
| 10,434,333 B2 * | 10/2019 | Liu | ......................... | H05H 3/06 |
| 10,537,750 B2 * | 1/2020 | Liu | ..................... | A61N 5/1049 |
| 10,556,127 B2 * | 2/2020 | Liu | ..................... | A61N 5/1082 |
| 10,568,964 B2 * | 2/2020 | Yamaguchi | ........... | A61N 5/1049 |
| 10,639,499 B2 * | 5/2020 | Liu | ......................... | G21K 1/10 |
| 10,744,345 B2 * | 8/2020 | Liu | ..................... | A61N 5/1042 |
| 10,773,104 B2 * | 9/2020 | Liu | ......................... | H05H 3/06 |
| 10,898,731 B2 * | 1/2021 | Liu | ..................... | A61N 5/1077 |
| 10,898,733 B2 * | 1/2021 | Liu | ..................... | A61N 5/1081 |
| 10,926,108 B2 * | 2/2021 | Liu | ..................... | A61N 5/1042 |
| 10,926,110 B2 * | 2/2021 | Liu | ......................... | A61N 5/10 |
| 11,058,898 B2 * | 7/2021 | Liu | ..................... | A61N 5/1064 |
| 11,198,023 B2 * | 12/2021 | Chen | .................... | G21K 5/04 |
| 11,224,766 B2 * | 1/2022 | Liu | ..................... | A61N 5/1077 |
| 11,266,859 B2 * | 3/2022 | Liu | ......................... | H05H 3/06 |
| 11,338,155 B2 * | 5/2022 | Hsiao | ..................... | H05H 3/06 |
| 11,400,314 B2 * | 8/2022 | Hsiao | ..................... | H05H 3/06 |
| 11,426,607 B1 * | 8/2022 | Hara | .................... | A61N 5/1049 |
| 11,458,336 B2 * | 10/2022 | Tsai | ..................... | A61N 5/1064 |
| 11,559,705 B2 * | 1/2023 | Chen | .................. | A61K 41/0095 |
| 11,561,308 B2 * | 1/2023 | Liu | ..................... | G01N 33/6803 |
| 11,583,701 B2 * | 2/2023 | Liu | ..................... | A61N 5/1077 |
| 11,740,370 B2 * | 8/2023 | Liu | ......................... | H05H 3/06 250/391 |
| 11,813,483 B2 * | 11/2023 | Liu | ......................... | A61N 5/10 |
| 11,826,583 B2 * | 11/2023 | Jiang | ..................... | G21G 4/02 |
| 12,023,524 B2 * | 7/2024 | Chen | .................. | A61N 5/1065 |
| 12,083,357 B2 * | 9/2024 | Honda | ................. | A61N 5/1048 |
| 12,194,318 B2 * | 1/2025 | Gong | .................. | A61N 5/1049 |

FOREIGN PATENT DOCUMENTS

| | | | |
|---|---|---|---|
| CN | 111686376 A | 9/2020 | |
| CN | 211675930 U | 10/2020 | |
| JP | 2000-288102 A | 10/2000 | |
| JP | WO 2023/190522 A1 * | 10/2023 | ............... A61N 5/10 |
| WO | 2019/116678 A1 | 6/2019 | |

* cited by examiner

TREATMENT PREPARATION APPARATUS COMPRISING A PERIPHERAL SIMULATOR AND TREATMENT EQUIPMENT FOR A BORON NEUTRON CAPTURE THERAPY (BNCT)

RELATED APPLICATIONS

The content of Japanese Patent Application No. 2021-053309, on the basis of which priority benefits are claimed in an accompanying application data sheet, is in its entirety incorporated herein by reference.

BACKGROUND

Technical Field

Certain embodiment of the present invention relates to a treatment preparation apparatus and a treatment equipment.

Description of Related Art

As a treatment system using radiation, a system described in the related art has been known. A treatment system described in the related art includes an irradiation chamber where irradiation is performed, and a preparation chamber for positioning a patient at the time of irradiation. In the preparation chamber, the patient is positioned with respect to an object, such as a bed, and the patient is fixed to the object. The patient is transported to the irradiation chamber together with the object in this state and is irradiated with radiation.

SUMMARY

According to one embodiment of the present invention, there is provided a treatment preparation apparatus that is provided in a preparation chamber for preparing for irradiation in an irradiation chamber for irradiating an irradiation target with radiation, including: an object to which the irradiation target is to be fixed so as to fix a relative position of the object to the irradiation target; and a peripheral simulator that simulates a peripheral portion of the object after the object is disposed in the irradiation chamber, when fixing the relative position of the object to the irradiation target in the preparation chamber.

According to another embodiment of the present invention, there is provided a treatment equipment including: an irradiation chamber equipped with an irradiation device that irradiates an irradiation target with a neutron ray; a preparation chamber for preparing for irradiation in the irradiation chamber; an object which is movable between the preparation chamber and the irradiation chamber, and to which the irradiation target is to be fixed so as to fix a relative position of the object to the irradiation target; and a peripheral simulator that simulates a peripheral portion of the object after the object is disposed in the irradiation chamber, when fixing the relative position of the object to the irradiation target in the preparation chamber.

DETAILED DESCRIPTION

Figure 1:
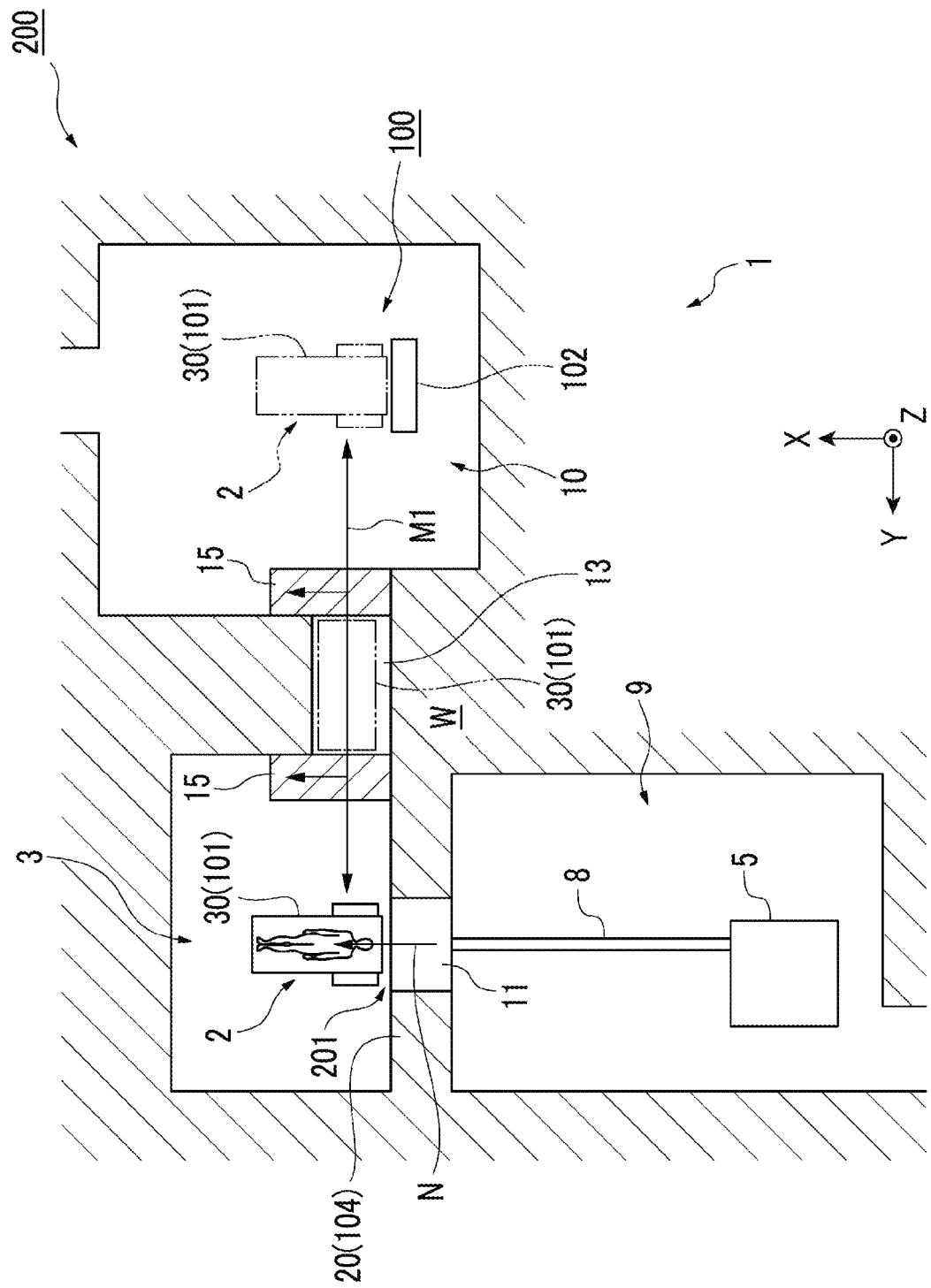
FIG. 1 is a schematic configuration diagram of a neutron capture therapy system to which a treatment preparation apparatus according to an embodiment of the present invention is applied.

Here, in the irradiation chamber, a structure such as a wall may be provided around an object such as a bed or a collimator. Such a structure is not considered in the alignment of the irradiation target in the preparation chamber, but when the irradiation target comes into contact with the structure in the irradiation chamber, the irradiation target may be shifted from the positioned state. Therefore, when positioning the irradiation target in the preparation chamber, it is required to position the irradiation target at a position where shift is unlikely to occur during irradiation.

It is desirable to provide a treatment preparation apparatus and a treatment equipment capable of positioning an irradiation target at a position where shift is unlikely to occur during irradiation, when positioning the irradiation target in the preparation chamber.

The treatment preparation apparatus includes an object to which the irradiation target is to be fixed so as to fix a relative position of the object to the irradiation target, in the irradiation chamber. Therefore, the irradiation target can be positioned with respect to the object in the preparation chamber such that the irradiation target can be treated at an appropriate position during irradiation. Here, the treatment preparation apparatus includes a peripheral simulator that simulates a peripheral portion of the object after the object is disposed in the irradiation chamber, when fixing the relative position between the object and the irradiation target in the preparation chamber. Therefore, when positioning the irradiation target in the preparation chamber, by using the peripheral simulator, the positioning can be performed in consideration of the peripheral portion of the object in the irradiation chamber. That is, in the preparation chamber, the irradiation target can be fixed at a position where shift is unlikely to occur in the irradiation chamber, considering the positional relationship between the irradiation target and the peripheral portion. From the above, when positioning the irradiation target in the preparation chamber, it is possible to position the irradiation target at a position that shift is unlikely to occur during irradiation.

The peripheral simulator may be a structure that simulates the peripheral portion. In this case, the peripheral simulator can simulate the peripheral portion with high reproducibility by using the structure.

The structure of the peripheral simulator may be movable with respect to the object. In this case, after completing the positioning of the irradiation target near the peripheral portion first, the structure is retracted from the vicinity of the object, and the other portion of the irradiation target can be positioned in a state where the work can be easily performed.

The peripheral simulator may include a sensor that detects contact with a structure and an output portion that outputs the detection result by the sensor. In this case, the positioning worker can easily identify that the irradiation target has come into contact with the structure.

The structure may include a pass-through portion corresponding to the irradiation path in the irradiation chamber.

In this case, the positioning worker can identify the state of the irradiation target from the pass-through portion, even if the structure is provided near the object.

In this case, the peripheral simulator may simulate the peripheral portion by non-physical means. In this case, the peripheral simulator can easily simulate the peripheral portion without providing a large-scale structure in the preparation chamber.

The peripheral simulator may include a sensor that detects that the irradiation target has come into contact with the peripheral portion in a simulated manner, and an output portion that outputs the detection result by the sensor. In this case, the positioning worker can easily identify that the irradiation target has come into contact with the peripheral portion in a simulated manner.

The non-physical means may be light of a color different from the color of the confirmation light for confirming the irradiation position of the irradiation target. In this case, it is possible to prevent the positioning worker from confusing the confirmation light for the irradiation position with the light used for simulating the peripheral portion.

The object may be selected from among a collimator, a bed, a chair, and an auxiliary fixation portion. In this case, an appropriate object can be selected according to the posture of the irradiation target in the irradiation chamber.

According to this treatment equipment, it is possible to achieve the same actions and effects as the above-described treatment preparation apparatus.

Hereinafter, embodiments for carrying out the present invention will be described in detail with reference to the accompanying drawings. In the description of the drawings, the same elements are designated by the same reference numerals, and duplicate description will be omitted.

The treatment preparation apparatus according to an embodiment of the present invention is utilized in a neutron capture therapy system. Therefore, first, the schematic configuration of the neutron capture therapy system will be described, and then the treatment preparation apparatus will be described. In the description of the drawings, the same elements are designated by the same reference numerals, and duplicate description will be omitted. Further, as shown in each figure, the X direction, the Y direction, and the Z direction which are orthogonal to each other may be set and used in the following description. In this case, the vertical direction is the Z direction, and the irradiation direction of the neutron ray N is the X direction.

First, the overall configuration of the neutron capture therapy system 1 will be described with reference to FIGS. 1 and 2. The neutron capture therapy system 1 is a system for performing boron neutron capture therapy (BNCT). The neutron capture therapy is a treatment method for treating a patient's lesion (for example, a tumor, or the like) by irradiating a patient Q (irradiation target) administered with boron ($^{10}B$) with a neutron ray.

The treatment equipment 200 includes an irradiation chamber 3 in which the patient Q placed on the treatment table 2 is accommodated and the patient Q is irradiated with a neutron ray N, an accelerator chamber 9 that accommodates an accelerator 5 that generates a charged particle beam P, and a transportation line 8 that transports the charged particle beam P emitted from the accelerator 5 to a neutron ray N generation unit 11 described later, and a neutron capture therapy system 1. The neutron capture therapy system 1 includes a neutron ray N generation unit 11 that receives a charged particle beam P from the transportation line 8 and generates a neutron ray N for irradiating the patient Q, and an accelerator 5. The neutron ray N generation unit 11 constitutes an irradiation device 201 that irradiates the patient Q with a neutron ray N. The accelerator 5 is, for example, a cyclotron that accelerates a charged particle (for example, a proton) and emits a charged particle beam P (for example, a proton beam). The accelerator 5 has the ability to emit a charged particle beam P having a beam radius of 40 mm and 60 kW (=30 MeV×2 mA), for example. The accelerator 5 is not limited to the cyclotron, and may be another accelerator such as a synchrotron, a linac, or an electrostatic accelerator. The irradiation chamber 3 and the accelerator chamber 9 are closed spaces surrounded by a blockade wall W, and the blockade wall W is a concrete wall for shielding radiation. The neutron ray N generation unit 11 is disposed so as to be embedded in the blockade wall W that separates the irradiation chamber 3 and the accelerator chamber 9. The neutron ray N generation unit 11 may be disposed in the irradiation chamber 3 without being embedded in the blockade wall W.

Further, the treatment equipment 200 includes a preparation chamber 10 adjacent to the irradiation chamber 3 in the Y direction. The preparation chamber 10 is isolated from the irradiation chamber 3 by the blockade wall W. A communication chamber 13 that allows passage between the irradiation chamber 3 and the preparation chamber 10 is provided so as to penetrate the blockade wall W. A shield door 15 that can be opened and closed is provided at the boundary between the communication chamber 13 and the irradiation chamber 3 and the boundary between the communication chamber 13 and the preparation chamber 10. The treatment table 2 can move in the Y direction between the irradiation chamber 3 and the preparation chamber 10 through the communication chamber 13. In the preparation chamber 10, preparatory work is performed prior to treatment. Examples of the preparatory work include work such as fixing (restraining) the patient Q to the treatment table 2 in a predetermined posture.

Figure 2:
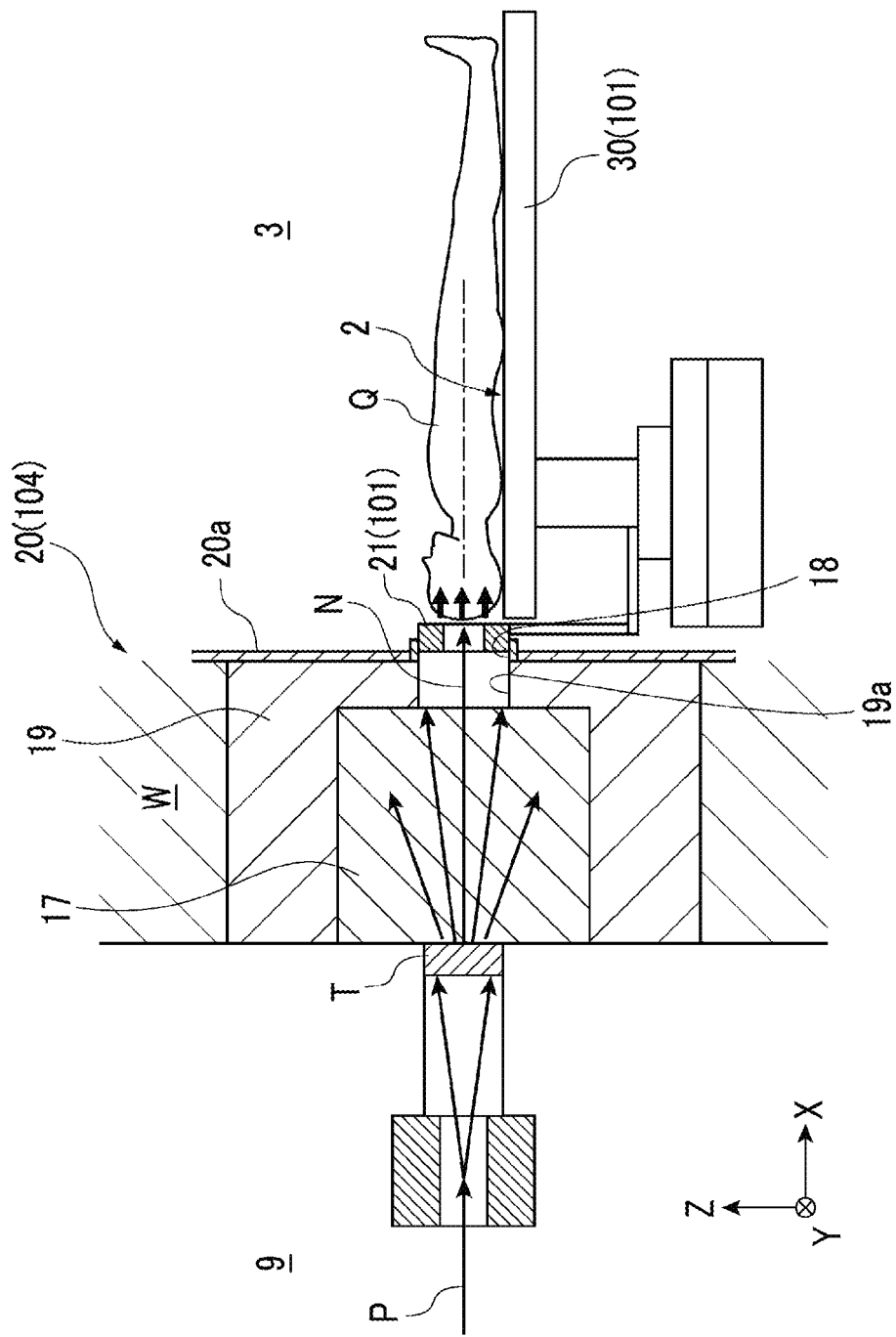
FIG. 2 is a schematic configuration diagram showing a state of an irradiation chamber.

As shown in FIG. 2, the neutron ray generation unit 11 includes a target T that generates a neutron ray N by being irradiated with a charged particle beam P, a deceleration member 17 that decelerates the generated neutron ray N (reduces energy), and a shield member 19 that covers at least a part of the periphery of the deceleration member 17 to shield radiation. The shield member 19 shields secondary radiation such as gamma ray generated by the deceleration member 17. The shield member 19 is formed with a through-hole 19a for allowing the neutron ray N to pass through. The wall portion that separates the irradiation chamber 3 and the accelerator chamber 9, such as the blockade wall W, the deceleration member 17, and the shield member 19, may be referred to as a partition wall 20. The neutron ray N emitted from the deceleration member 17 passes through the collimator 21 provided on the treatment table 2 and is applied to the patient Q. The collimator 21 can change the irradiation range of the neutron ray N to be applied to the patient Q. The collimator 21 is attached to the wall surface 20a of the partition wall 20 on the irradiation chamber 3 side. The partition wall 20 is formed with an irradiation port 18 which is an opening for emitting a neutron ray N that has passed through the through-hole 19a and irradiating the patient Q. The collimator 21 is attached to the irradiation port 18. In the example shown in FIG. 2, the collimator 21 is fitted in the irradiation port 18.

In FIG. 2, the patient Q on the treatment table 2 is in the recumbent position, but the patient Q in the sitting position may be irradiated with the neutron ray N (see FIG. 5 described later). Depending on the position of the lesion of the patient Q, the patient's posture may be set in the sitting position in order to bring the lesion closer to the collimator 21. In the following embodiment, a case where the patient Q in the sitting position is irradiated with the neutron ray N will be described.

In the neutron capture therapy by the neutron capture therapy system 1, a treatment planning for determining the distribution and intensity of the neutron ray to be applied to the patient Q is created. Since it is necessary to appropriately irradiate the lesion of patient Q with a neutron ray, the posture of patient Q is also an important factor in the treatment planning. Therefore, in the preparation chamber 10 (see FIG. 1) shown in FIG. 1, the posture of the patient Q at the time of treatment in the irradiation chamber 3 is adjusted so as to follow the planning.

Figure 3:
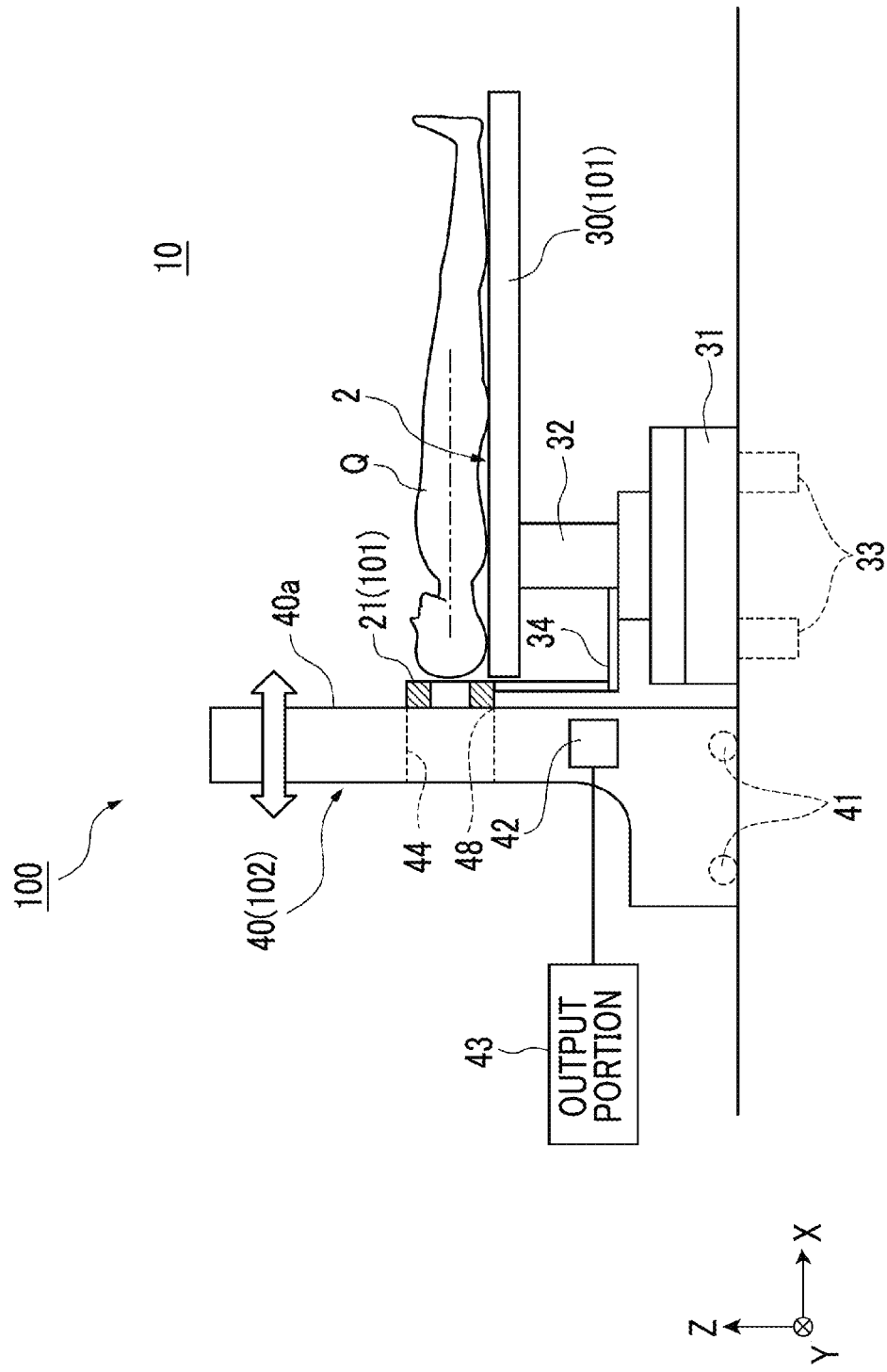
FIG. 3 is a schematic configuration diagram showing the treatment preparation apparatus.

Next, the treatment preparation apparatus 100 according to the present embodiment will be described with reference to FIGS. 1 and 3. The treatment preparation apparatus 100 is an apparatus provided in the preparation chamber 10 for preparing for irradiation in the irradiation chamber 3 for irradiating the patient Q with the neutron ray N. As shown in FIGS. 1 and 3, the treatment preparation apparatus 100 includes an object 101 and a peripheral simulator 102.

The object 101 is an object to which the patient Q is to be fixed so as to fix a relative position of the object to the patient Q, in the irradiation chamber 3. In the present embodiment, the bed 30 of the treatment table 2 and the collimator 21 are selected as the object 101. The bed 30 is a member on which the patient Q is placed in a laid state. As shown in FIG. 3, the bed 30 is supported by the base portion 31 via the support portion 32. The base portion 31 is movably disposed on the floor along the guide portion 33. The guide portion 33 extends from the preparation chamber 10 to the irradiation chamber 3 via the communication chamber 13. Thereby, the treatment table 2 having the bed 30 can reciprocate between the preparation chamber 10 and the irradiation chamber 3 along the movement path M1 (see FIG. 1) passing through the communication chamber 13.

The support portion 32 extends upward from the base portion 31 and supports the bed 30 at the upper end. A support bar 34 that supports the collimator 21 is connected to the lower end of the support portion 32. The bed 30, the collimator 21, the support portion 32, and the support bar 34 can rotate in the XY plane while being supported by the base portion 31. As shown in FIG. 1, at the time of irradiation in the irradiation chamber 3, the bed 30 is disposed at an arbitrary angle with respect to the collimator 21. Therefore, even when the patient Q is positioned in the preparation chamber 10, the bed 30 is disposed at an arbitrary angle with respect to the collimator 21. When the bed 30 moves from the preparation chamber 10 to the irradiation chamber 3, the bed is rotated by 90° such that the bed can pass through the communication chamber 13, and is in a state of having a longitudinal direction in the Y axial direction.

As shown in FIG. 3, the peripheral simulator 102 simulates the peripheral portion 104 of the object 101 after the object 101 is disposed in the irradiation chamber 3, when fixing the relative position of the object 101 to the patient Q in the preparation chamber 10. The peripheral portion 104 of the object 101 is an object existing around the object 101, and is an object that may come into contact with the patient Q due to the patient Q changing his or her posture, reaching out, or the like. In the present embodiment, the partition wall 20 existing around the collimator 21 and the bed 30 corresponds to the peripheral portion 104 (see FIG. 2). The peripheral portion 104 includes a wall surface 20a which is a portion extending from the collimator 21 in the irradiation chamber 3 in a direction (Y axial direction, Z axial direction) intersecting the irradiation direction (X axial direction). The peripheral simulator 102 is composed of a simulated wall structure 40 which is a structure simulating a partition wall 20 (see FIG. 2). The simulated wall structure 40 does not need to simulate the entire partition wall 20, and may at least simulate the portion of the partition wall 20 that may come into contact with the patient Q. Therefore, the simulated wall structure 40 has a wall surface 40a that simulates the wall surface 20a of the partition wall 20 in the region around the mounting position of the collimator 21. The height and thickness of the simulated wall structure 40 is smaller than the height and thickness of the partition wall 20. Further, the simulated wall structure 40 is provided only in a part around the bed 30 in the Y axial direction (see FIG. 1).

The simulated wall structure 40 of the peripheral simulator 102 is movable with respect to the object 101. The simulated wall structure 40 can reciprocate in the X axial direction, is disposed at a position close to the collimator 21 when positioning the patient Q, and can move so as to be separated to the negative side in the X axial direction from the collimator 21, when the positioning is completed. The simulated wall structure 40 has a moving mechanism 41 such as wheels that can travel on the floor. The wheels of the moving mechanism 41 may be configured to switch contact and non-contact with the floor surface by operating a lever or the like.

The peripheral simulator 102 may include a sensor 42 that detects contact with the simulated wall structure 40, and an output portion 43 that outputs a detection result by the sensor 42. With respect to the sensor 42, the sensor type is not particularly limited as long as the sensor can detect that the patient Q has come into contact with the simulated wall structure 40, non-contact type sensors (sensors using light such as a laser, ultrasonic waves, radar, radio waves, or the like) may be used, or contact type sensors (sensors using pressure detection or the like) may be used. The output portion 43 may output a warning sound or output the warning content to the monitor, when the patient Q comes into contact with the simulated wall structure 40. However, the output method and output content of the output portion 43 are not particularly limited as long as it can be known that the patient Q has come into contact with the simulated wall structure 40.

The simulated wall structure 40 includes a pass-through portion 44 corresponding to the irradiation path in the irradiation chamber 3. The pass-through portion 44 penetrates the simulated wall structure 40 in the X axial direction at a position corresponding to the through-hole of the collimator 21. The pass-through portion 44 simulates the through-hole 19a (FIG. 2) of the shield member 19, as an irradiation path through which the neutron ray N passes in the partition wall 20. The opening 48 near the wall surface 40a, of the pass-through portion 44, simulates the irradiation port 18 (FIG. 2). In FIG. 3, the collimator 21 is attached to the simulated wall structure 40 so as to be pressed against the opening 48, but the collimator 21 may be attached to the simulated wall structure 40 so as to be fitted into the opening 48. The pass-through portion 44 is a portion that functions as a peephole during the positioning work of the patient Q. Therefore, since the pass-through portion 44 may be closed at times other than the positioning work, a lid portion or the like having a double door structure may be provided.

Next, the actions and effects of the treatment preparation apparatus 100 according to the present embodiment will be described.

The treatment preparation apparatus 100 includes an object 101 to which the patient Q is to be fixed so as to fix a relative position of the object to the patient Q, in the irradiation chamber 3. Therefore, the patient Q can be positioned with respect to the object 101 in the preparation chamber 10 such that the patient Q can be treated at an appropriate position during irradiation.

Here, as a comparative example, a neutron capture therapy system in the case where the peripheral simulator 102 is not provided in the preparation chamber 10 will be described. In this case, the patient Q needs to maintain the same posture for a long period of time, and may try to take a comfortable posture. For example, the patient Q may move body parts other than the affected part. For example, the patient Q may place his arm on the collimator 21. When the patient Q is transported to the irradiation chamber 3 together with the object 101 in this state, the arm of the patient Q may come into contact with the partition wall 20 and the irradiation position may shift. When the patient Q is shifted in this way, it becomes necessary for the worker to enter the irradiation chamber 3 to perform the positioning work.

On the other hand, in the treatment preparation apparatus 100 according to the present embodiment, the treatment preparation apparatus 100 includes a peripheral simulator 102 that simulates a peripheral portion 104 of the object 101 after the object 101 is disposed in the irradiation chamber 3, when fixing the relative position of the object 101 to the irradiation target in the preparation chamber 10. Therefore, when positioning the patient Q in the preparation chamber 10, by using the peripheral simulator 102, the positioning can be performed in consideration of the peripheral portion 104 of the object 101 in the irradiation chamber 3. That is, in the preparation chamber 10, the patient Q can be fixed at a position in the irradiation chamber 3 where shift is unlikely to occur, considering the positional relationship between the patient Q and the peripheral portion 104. From the above, when positioning the patient Q in the preparation chamber 10, it is possible to position the patient Q at a position that shift is unlikely to occur during irradiation. Thus, it is not necessary for the worker to enter the irradiation chamber 3 to perform the positioning work, so that the exposure can be reduced.

The peripheral simulator 102 may be a simulated wall structure 40 that simulates the peripheral portion 104. In this case, the peripheral simulator 102 can simulate the partition wall 20 which is the peripheral portion 104 with high reproducibility by using the simulated wall structure 40.

The simulated wall structure 40 of the peripheral simulator 102 may be movable with respect to the object 101. In this case, after completing the positioning of the patient Q near the peripheral portion 104 first, the simulated wall structure 40 is retracted from the vicinity of the object 101, and the other portion of the patient Q can be positioned in a state where the work can be easily performed.

The peripheral simulator 102 may include a sensor 42 that detects contact with the simulated wall structure 40, and an output portion 43 that outputs a detection result by the sensor 42. In this case, the positioning worker can easily identify that the patient Q has come into contact with the simulated wall structure 40.

The simulated wall structure 40 may include a pass-through portion 44 corresponding to the irradiation path in the irradiation chamber 3. In this case, the positioning worker can identify the state of the patient Q from the pass-through portion 44 even if the simulated wall structure 40 is provided near the object 101.

The treatment equipment 200 includes an irradiation chamber 3 equipped with an irradiation device 201 that irradiates an irradiation target with a neutron ray, a preparation chamber 10 for preparing for irradiation in the irradiation chamber 3, an object 101 which is movable between the preparation chamber 10 and the irradiation chamber 3, and to which the irradiation target is to be fixed so as to fix a relative position of the object to the irradiation target, and a peripheral simulator 102 that simulates a peripheral portion 104 of the object 101 after the object 101 is disposed in the irradiation chamber 3, when fixing the relative position of the object 101 to the irradiation target in the preparation chamber 10.

According to this treatment equipment 200, it is possible to achieve the same actions and effects as the above-described treatment preparation apparatus 100.

In neutron capture therapy, the patient is brought as close to the collimator 21 as possible in order to raise the effective dose. The collimator 21 may be disposed to be embedded in the wall surface during treatment. At that time, a body part (arm, or the like) other than the treatment site may hit the wall and the irradiation position may shift. Therefore, a unit that simulates the peripheral shape of the object for fixing the patient is provided. Therefore, the patient (other than the affected part) can be disposed at a position where the position of the affected part does not shift during treatment.

When the treatment equipment 200 employs a treatment process that takes steps from the preparation chamber 10 to the irradiation chamber 3, the fixation is completed at the treatment preparation stage, so that the worker does not need to enter the treatment chamber and low exposure can be achieved. Without this unit, the worker needs to eventually enter the treatment chamber to perform fixing work.

The present invention is not limited to the above-described embodiment.

Figure 4:
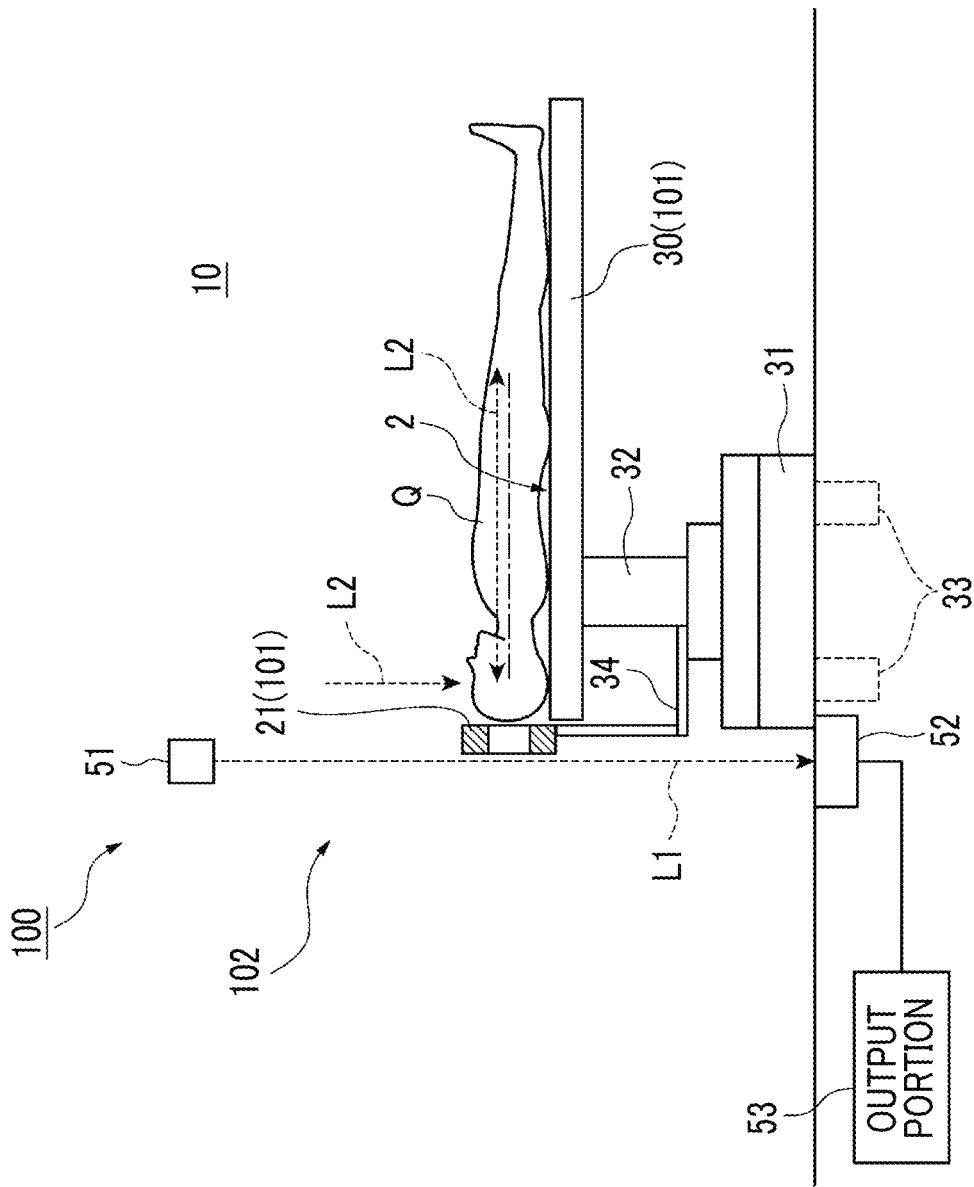
FIG. 4 is a schematic configuration diagram showing a treatment preparation apparatus according to a modification example.

For example, as shown in FIG. 4, the peripheral simulator 102 may simulate the partition wall 20 which is the peripheral portion 104 by non-physical means. Specifically, the peripheral simulator 102 has an oscillator 51 that oscillates the non-physical means. The non-physical means is means that can be used for various measurements and detections such as colored light, ultrasonic waves, radar, and radio waves. In FIG. 4, colored light L1 is used as the non-physical means. The oscillator 51 oscillates the colored light L1 such that the colored light L1 is disposed at a position corresponding to the wall surface 20a of the partition wall 20. The oscillator 51 may be attached in any way in the preparation chamber 10, and for example, the oscillator 51 may be attached to the ceiling or wall portion of the preparation chamber 10, may be attached to a dedicated jig, or may be attached to the object 101. A plurality of oscillators 51 may be provided such that the colored light L1 is disposed at a predetermined pitch at a position corresponding to the wall surface 20a. Although the colored light L1 is oscillated from top to bottom, the colored light L1 may be oscillated from bottom to top, or may be oscillated in a lateral direction or an oblique direction. Alternatively, when the collimator 21 is provided with the oscillator 51, the colored light L1 may be oscillated radially from the center axis of the collimator 21. The peripheral simulator 102 may simulate the partition wall 20 as long as the affected part of the patient Q is fixed to the collimator 21 and the body part of the patient Q can be moved.

As described above, the peripheral simulator 102 may simulate the peripheral portion 104 by non-physical means. In this case, the peripheral simulator 102 can easily simulate the peripheral portion 104 without providing a large-scale structure in the preparation chamber 10.

The peripheral simulator 102 may include a sensor 52 that detects that the patient Q has come into contact with the peripheral portion 104 in a simulated manner, and an output portion 53 that outputs the detection result by the sensor 52. In this case, the positioning worker can easily identify that the patient Q has come into contact with the peripheral portion 104 in a simulated manner. The sensor 52 is provided at a position facing the oscillator 51, and is provided on the floor in the example shown in FIG. 4. The sensor 52 and the output portion 53 may be omitted. For example, when the colored light L1 is used as non-physical means, it is possible for the worker to identify that the patient Q has come into contact with the peripheral portion 104 in a simulated manner by confirming that the colored light L1 is interrupted by the patient Q.

The colored light L1 which is the non-physical means may be light having a color different from the color of the confirmation light L2 for confirming the irradiation position of the patient Q. In this case, it is possible to prevent the positioning worker from confusing the confirmation light L2 for the irradiation position with the colored light L1 simulating the peripheral portion 104.

Here, the object 101 may be selected from among a collimator, a bed, a chair, and an auxiliary fixation portion. In this case, an appropriate object 101 can be selected according to the posture of the patient Q in the irradiation chamber 3. In the above-described embodiment, since the treatment is performed with the patient Q in the recumbent position, the collimator and the bed are selected as the object 101. On the other hand, when the treatment is performed with the patient Q in the sitting position, a chair may be selected instead of the bed as the object 101, and an auxiliary fixation portion may be further selected.

Figure 5:
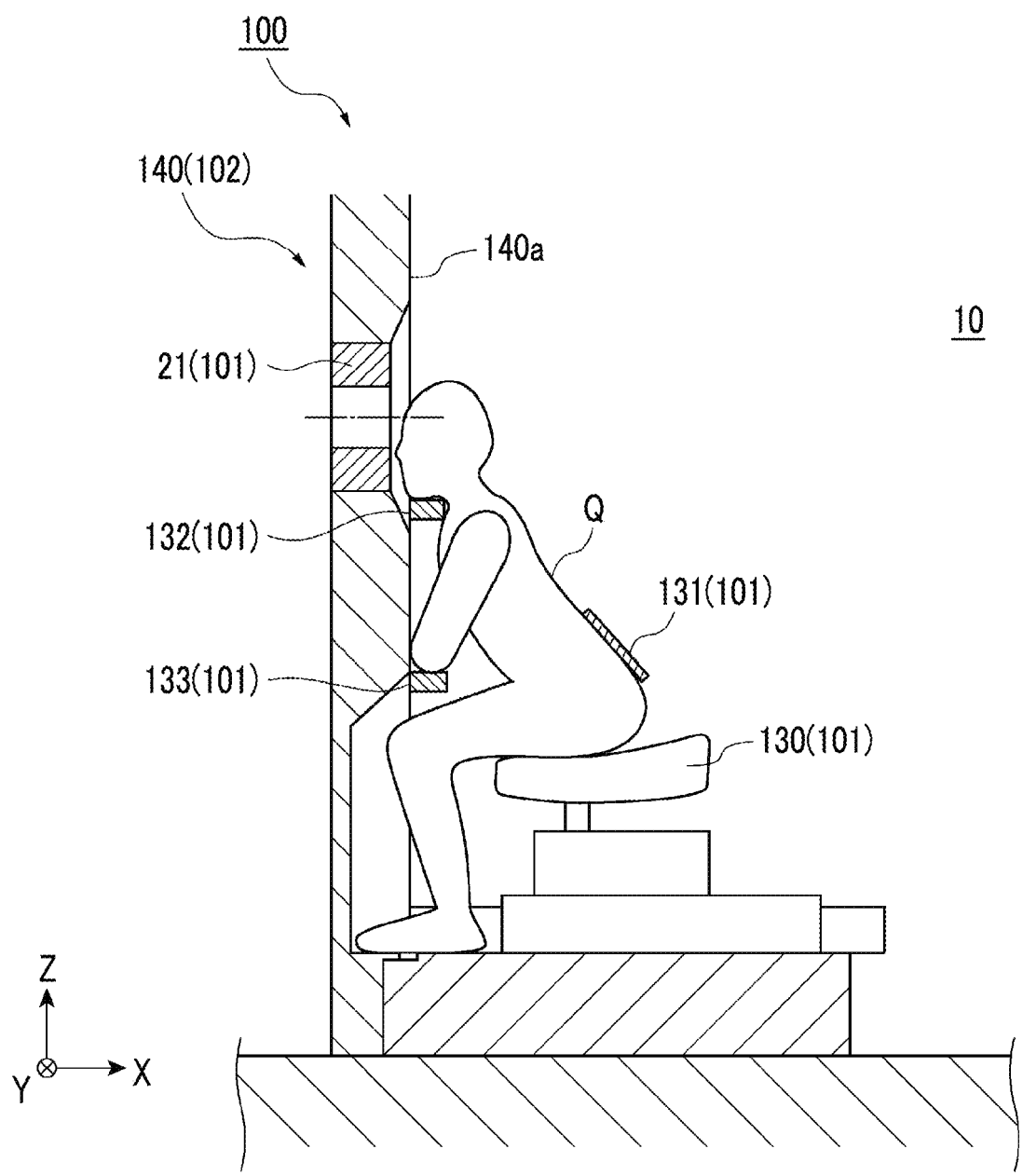
FIG. 5 is a schematic configuration diagram showing a treatment preparation apparatus according to another modification example.

Specifically, the treatment preparation apparatus 100 as shown in FIG. 5 may be adopted. As shown in FIG. 5, the collimator 21 and the chair 130 are selected as the object 101, and the waist support member 131, the chin rest member 132, and the elbow support member 133, which are auxiliary fixation portions, are adopted. The collimator 21, the waist support member 131, the chin rest member 132, and the elbow support member 133 are supported by support member (not shown) and can be moved to the irradiation chamber 3 together with the chair 130. The simulated wall structure 140 has a wall surface 140a shaped to fit the body part of the patient Q sitting on the chair 130. For example, the wall surface 140a has a recess at a position corresponding to the foot of the patient Q.

What is applied to the patient is not limited to a neutron ray, and the treatment preparation apparatus of the present invention can be applied as long as the system irradiates the patient with the fixed posture.

It should be understood that the invention is not limited to the above-described embodiment, but may be modified into various forms on the basis of the spirit of the invention. Additionally, the modifications are included in the scope of the invention.

What is claimed is:

1. A treatment preparation apparatus that is provided in a preparation chamber for preparing for an irradiation in an irradiation chamber for irradiating an irradiation target with a neutron ray, comprising:
   an object to which the irradiation target is to be fixed so as to fix a relative position of the irradiation target to the object; and
   a peripheral simulator that simulates a peripheral portion of the object after the object is disposed in the irradiation chamber, when fixing the relative position of the irradiation target to the object in the preparation chamber,
   wherein the peripheral simulator is a structure simulating the peripheral portion, and
   the peripheral simulator includes a sensor that detects a contact with the structure, and an output portion that outputs a detection result by the sensor.

2. The treatment preparation apparatus according to claim 1, wherein
   the structure of the peripheral simulator is movable with respect to the object.

3. The treatment preparation apparatus according to claim 1, wherein
   the structure includes a pass-through portion corresponding to an irradiation path in the irradiation chamber.

4. The treatment preparation apparatus according to claim 1, wherein
   the object is selected from among a collimator, a bed, a chair, and an auxiliary fixation portion.

5. A treatment equipment comprising:
   an irradiation chamber comprising an irradiation device that irradiates an irradiation target with a neutron ray;
   a preparation chamber for preparing for an irradiation in the irradiation chamber;
   an object which is movable between the preparation chamber and the irradiation chamber, and to which the irradiation target is to be fixed so as to fix a relative position of the irradiation target to the object; and
   a peripheral simulator that simulates a peripheral portion of the object after the object is disposed in the irradiation chamber, when fixing the relative position of the irradiation target to the object in the preparation chamber,
   wherein the peripheral simulator is a structure simulating the peripheral portion, and
   the peripheral simulator includes a sensor that detects a contact with the structure, and an output portion that outputs a detection result by the sensor.

6. A treatment preparation apparatus that is provided in a preparation chamber for preparing for an irradiation in an irradiation chamber for irradiating an irradiation target with a neutron ray, comprising:
   an object to which the irradiation target is to be fixed so as to fix a relative position of the irradiation target to the object; and
   a peripheral simulator that simulates a peripheral portion of the object after the object is disposed in the irradiation chamber, when fixing the relative position of the irradiation target to the object in the preparation chamber,
   wherein the peripheral simulator simulates the peripheral portion by non-physical means.

7. The treatment preparation apparatus according to claim 6, wherein
   the peripheral simulator includes a sensor that detects that the irradiation target has come into a contact with the peripheral portion in a simulated manner, and an output portion that outputs a detection result by the sensor.

8. The treatment preparation apparatus according to claim 6, wherein
   the non-physical means is light having a color different from a color of confirmation light for confirming an irradiation position of the irradiation target.

9. A treatment equipment comprising:
   an irradiation chamber comprising an irradiation device that irradiates an irradiation target with a neutron ray;
   a preparation chamber for preparing for an irradiation in the irradiation chamber;

an object which is movable between the preparation chamber and the irradiation chamber, and to which the irradiation target is to be fixed so as to fix a relative position of the irradiation target to the object; and a peripheral simulator that simulates a peripheral portion of the object after the object is disposed in the irradiation chamber, when fixing the relative position of the irradiation target to the object in the preparation chamber, wherein the peripheral simulator simulates the peripheral portion by non-physical means.

* * * * *